United States Patent
Tkatchouk et al.

[11] Patent Number: 5,207,623
[45] Date of Patent: May 4, 1993

[54] ERGOMETRIC DEVICE

[75] Inventors: Elena N. Tkatchouk; Tatiana N. Tsyganova, both of Moscow, U.S.S.R.; Regula Staebler, Vernier S, Switzerland

[73] Assignee: Tradotec S.A., Geneva, Switzerland

[21] Appl. No.: 898,072

[22] Filed: Jun. 12, 1992

[30] Foreign Application Priority Data
Jun. 12, 1991 [EP] European Pat. Off. ........ 91810445.6

[51] Int. Cl.$^5$ .......................... A63B 69/16; A61B 5/08
[52] U.S. Cl. ...................................... 482/61; 482/900; 128/725
[58] Field of Search ............... 482/57, 1, 13; 128/725, 128/720, 205.11, 205.27

[56] References Cited
U.S. PATENT DOCUMENTS

| | | | |
|---|---|---|---|
| 3,674,022 | 7/1972 | Dounoucos | 128/205.27 |
| 4,034,743 | 7/1977 | Greenwood et al. | 128/725 |
| 4,086,923 | 5/1978 | Henkin | 128/205.11 |
| 4,463,764 | 8/1984 | Anderson et al. | 128/725 |
| 5,005,582 | 4/1991 | Serikov et al. | 128/725 |

FOREIGN PATENT DOCUMENTS

| | | | |
|---|---|---|---|
| 1456161 | 2/1989 | U.S.S.R. | 128/205.11 |
| 8505280 | 12/1985 | World Int. Prop. O. | 482/57 |

*Primary Examiner*—Stephen R. Crow
*Attorney, Agent, or Firm*—Robert E. Burns; Emmanuel J. Lobato

[57] ABSTRACT

The ergometric device has an ergometric stationary bicycle exerciser, a hypoxic gas generator, a mask, and a flexible hose connecting the generator to the mask. The user of the device sits on the saddle of the exerciser, and produces his effort by inhaling, through the mask, the hypoxic mixture. His ECG, his pulse rate and his blood pressure appear on the screen of the generator.

6 Claims, 3 Drawing Sheets

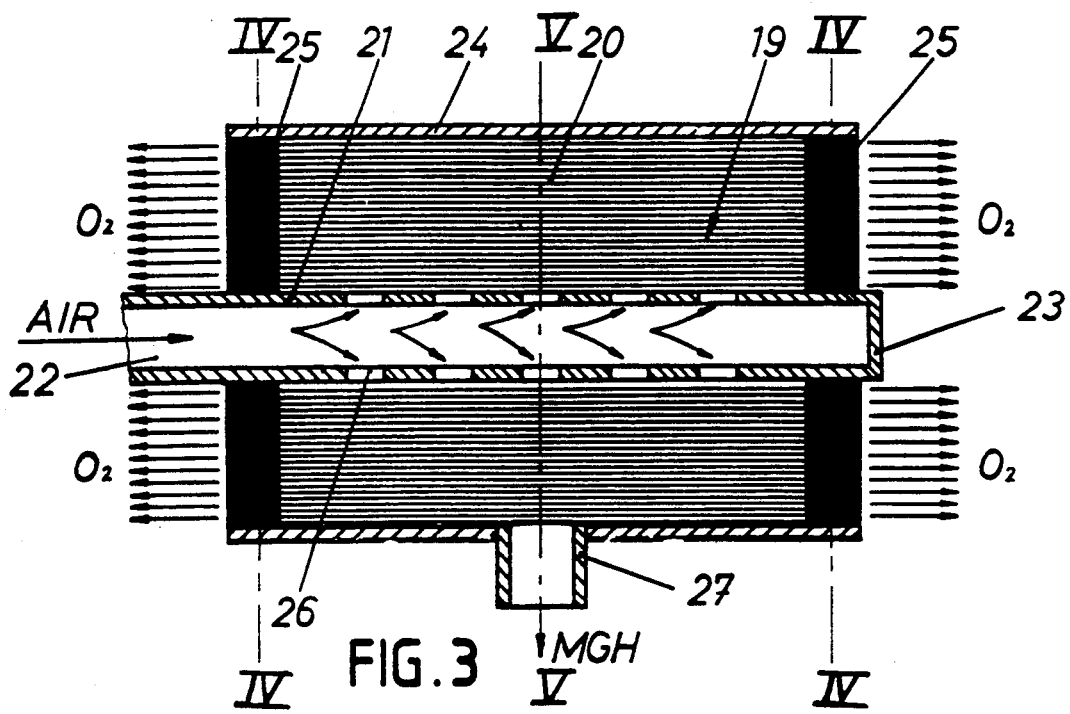
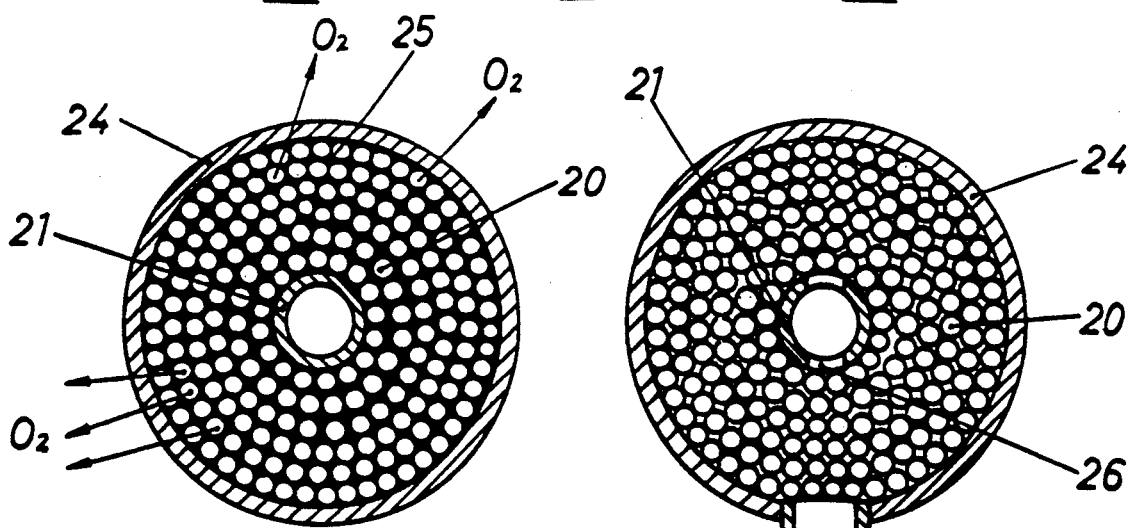
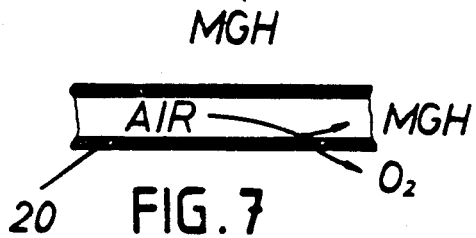

ERGOMETRIC DEVICE

FIELD OF THE INVENTION

The invention relates to an ergometric device including an apparatus enabling persons to perform physical exercises, either in view of training or to keep fit, or as a therapeutic measure when these persons suffer from cardio-vascular ailments, pulmonary ailment, and the like.

BACKGROUND OF THE INVENTION

An apparatus of this type, particularly a stationary bicycle imitating road loads, is known to be provided with means for adjusting the intensity of this load: see U.S. Pat. No. 3,871,648.

An apparatus of this type enabling one to make repeating physical exercises, including a seat and a handle bar, is further known to be provided with means to adjust the load to be attained by its user: see U.S. Pat. No. 4,079,931.

It is also known from U.S. Pat. No. 4,441,705 to provide such an apparatus in which the user drives a wheel fitted with adjustable braking means.

The disadvantage of these apparatuses is that it is impossible to prevent overloads and to provide loads within safe limits, particularly in the case of a person suffering from pathologies of the system of the cardio-vascular, pulmonary or other types.

OBJECTS AND SUMMARY OF THE INVENTION

The ergometric device according to the present invention comprises an apparatus similar to the above-noted ones, and enables a person, athletic or not, to expend physical energy in measured and controlled quantities, during an adjustable time lapse, while reducing the hazards associated with exceeding the programmed safe load limits so as to make the latter safer, in particular for persons who suffer from pathologies of the system of the cardiovascular, pulmonary, gastro-intestinal, neuralgic, dermatologic or gynecologic types.

In view thereof, this device is characterized in that said apparatus is associated with a generator of hypoxic gas mixtures, i.e. having from 9 to 16% of oxygen and from 84 to 91% nitrogen, in volume, a mask destined to be applied on the user's face, and connecting means between said generator and said mask so that the user inhales this hypoxic mixture when expending his effort. Inhalation of the hypoxic mixture may be continuous, discontinuous or alternated with air.

The outcome of this inhalation, made in a controlled fashion, and as evidenced by numerous tests, is the reduction of the risks associated with overloads and to the making safer of the limit loads, during the physical training of persons in good health, athletes for example, as well as for exercises performed by subjects suffering from the above-noted pathologies. The continuous or discontinuous inhalation of the hypoxic mixture, or still its alternating with air breathing, programmed in a well defined fashion in each case, provides the following advantages:

improvement of the resistance of the system to short or excessive overloads;

adaptation of the system to the stress associated with these overloads;

increase of the oxygen-carrying capability of the blood.

These various effects promote an improved stability of the energy metabolism to thus enable the oxygen consumed by the user to be more efficiently used, in particular about its vital organs.

The oxygennitrogen level of the hypoxic gas mixture will obviously be adjusted as a function of the physical loads to be attained by the subject and of the adaptation of his system to this mixture.

Experiments have shown that this method is not only effective for persons in good health, for example athletes, but has also remarkable results, from a therapeutic point of view, on persons suffering from cardio-vascular, pulmonary, gastro-intestinal, neuralgic, dermatologic and gynecologic pathologies. In these cases, the measured and controlled physical loads, and the inhalation of a hypoxic gas mixture, will invigorate the system, providing a longer remission of pathologies and increasing the resistance of the system.

The inhalation programme of the hypoxic mixture may for example provide periods of from 2 to 15 minutes, separated by intervals of from 2 to 5 minutes of air breathing, so as to reestablish the respiratory functions and to increase the oxygen levels inside the lungs. The inhalation period of the hypoxic gas mixture and of the physical loads can be gradually increased, from 15 to 60 minutes, daily, for a complete treatment of 10 to 30 days.

BRIEF DESCRIPTION OF THE DRAWINGS

The accompanying drawings illustrate schematically and by way of example, a preferred embodiment of the invention as well as a variant of a detail.

Figure 1:
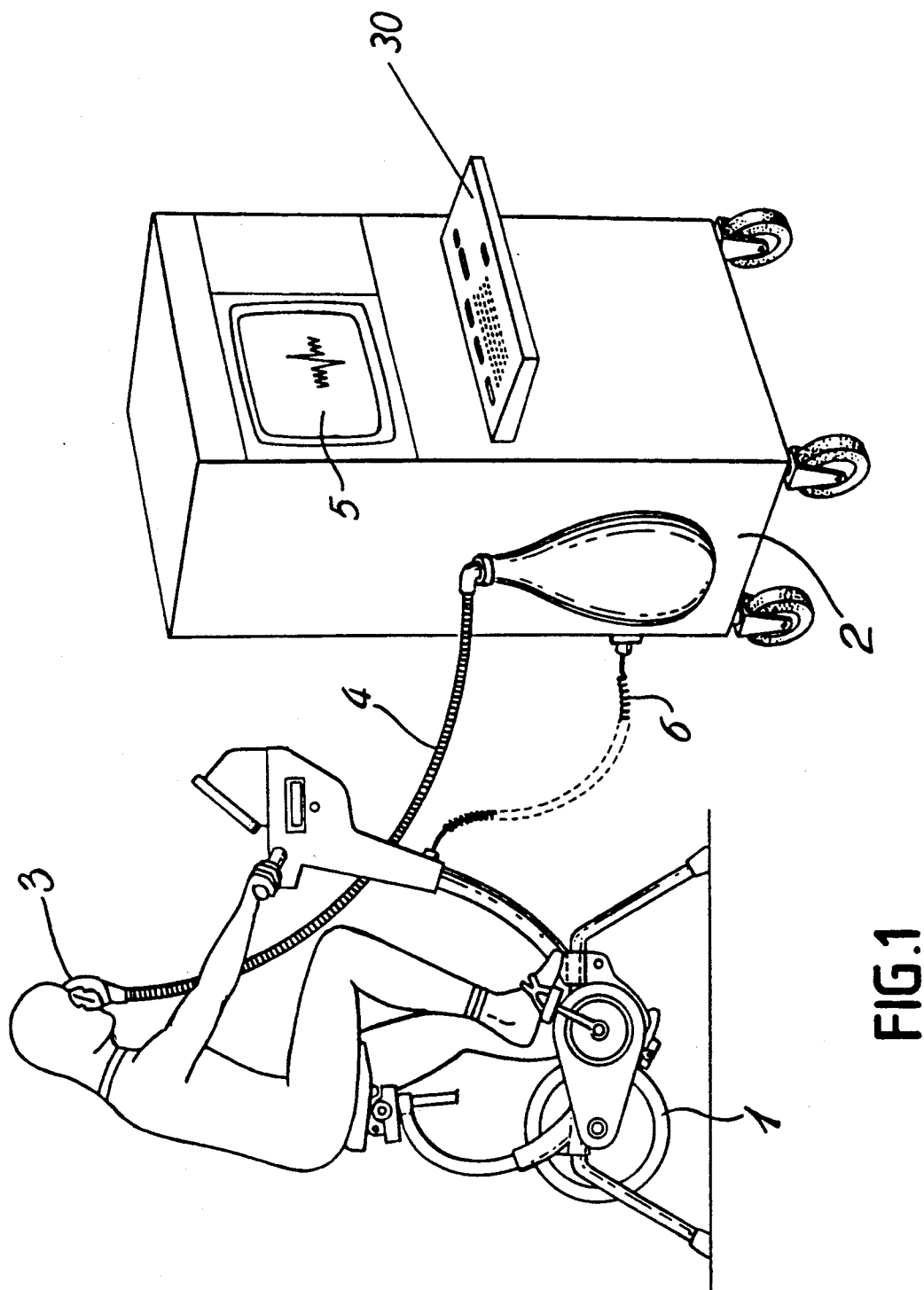
Figure 2:
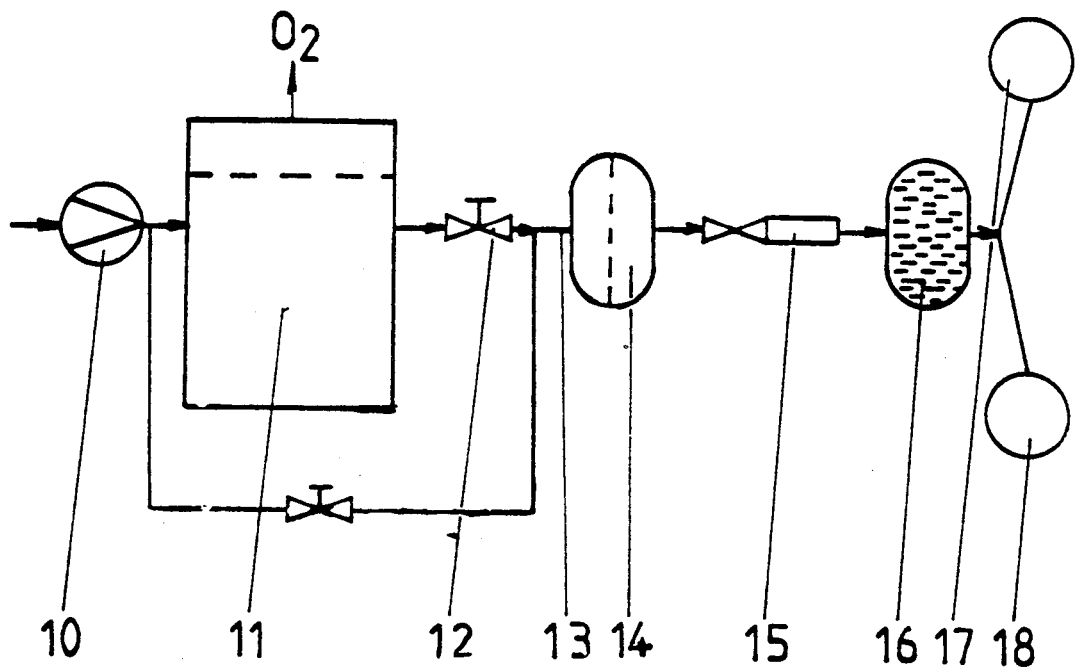

IN THE DRAWINGS:

FIG. 1 is a schematic perspective view of apparatus in accordance with the invention, showing a user of the apparatus, FIG. 2 is a block diagram of a hypoxic gas mixture generator of the apparatus, FIG. 3 is an axial section of an oxygen depleting unit of the hypoxic gas mixture generator, FIG. 4 is a cross-section on the line IV—IV in FIG. 3, FIG. 5 is a cross-section on the line V—V in FIG. 3

FIG. 6 is a longitudinal section of a fiber of the oxygen depleting unit, and

FIG. 7 is a view like FIG. 6 but showing a variation.

DESCRIPTION OF PREFERRED EMBODIMENT

The device shown comprises a stationary ergometric bicycle exerciser 1, provided with load adjusting means, with a hypoxic gas mixture generator 2 and with a mask 3, being adjustable on the user's face and connected to the generator 2 by a flexible hose 4.

Generator 2, which may provide a hypoxic gas mixture having from 9 to 16% of oxygen and from 84 to 91% of nitrogen, comprises, installed on a carriage, a membrane compressor 10, a gas separation unit 11, control valves 12 and 13, a filter 14 to retain eventual contaminants, a rotometer 15 and a gas mixture humidifier 16, a receptor 17 and a mask 18 for the patient. On the front face of the carriage frame there is a keyboard 30 providing means enabling the programming of the treatment and means adjusting the components of the hypoxic gas mixture, as well as a screen 5 onto which are visualized the ECG of the user, his pulse rate and his blood pressure, corresponding data being transmitted through a sensor mounted on the user and through a flexible connector 6.

The gas separation unit 11 (FIGS. 3-7) comprises a bundle 19 of hollow polymeric fibers 20 based on poly 4-methyl-pentene-1 having a wall thickness of 12-30 microns and an internal diameter of 8 to 20 microns.

The bundle 19 extends longitudinally between a tube 21 of which one end 22 is open and the other end 23 is closed and an impervious cylindrical case 24, which is open at both ends.

Material 25 impregnating the exterior surfaces of the hollow fibers 20 at the two ends of the bundle 19 seals the interestices between the hollow fibers. Thus only the interiors of the hollow fibers 20, open at their two ends, communicate with the exterior.

The tube 21 has longitudinally spaced openings 26 and the cylindrical case 24 has an orifice 27 which puts the space containing the fibers into communication with the control valve 12.

The air which the compressor 10 forces into the unit 11 through the open end 22 of the tube 21 passes out through the openings 26 and penetrates the bundle 19 where it enters into contact with the fibers 20.

Under the action of the pressure prevailing in the interior of the cylindrical case 24, the oxygen and the nitrogen of the air pass through the micropores of the walls of the fibers 20 in a selective manner, the selectivity being explained by the chemical properties of the hollow fibers (see FIG. 6) in the manner that the flow of compressed air entering the unit 11 is divided, in the bundle 19, into a flow of oxygen which flows to the interior of the fibers 20 and is evacuated through the open ends of the fibers at the ends of the cylindrical case 24 and a flow consisting of a hypoxic-mixture (MGH) which passes out through the orifice 27 and hence through the control valve 12 to the filter 14, rotameter 15, humidifier 16 to the receptor 17 and mask 18.

The hypoxic gas mixture provided by the generator 2 reaches the face of the user through the mask 3 and the hose 4. Sitting on the saddle of the bicycle 1, the user expends energy by pedalling while inhaling the hypoxic mixture in a continuous or discontinuous fashion, or alternately with air breathing by closing valve 12 and opening bypass valve 12a, according to a defined program.

A person in good health, for example an athlete, using the device for his physical training or to keep in shape, may be pedalling at speeds of about 60 rpm, with defined loads based on limits corresponding to his age, his weight and his physical condition.

The power of these loads may for example range from 10 watts at the beginning, to 15 watts as soon as the 10th day, and to 25 watts from the 20th day.

When pedalling out, the user will inhale, for example during 15 to 45 minutes, a hypoxic mixture consisting, by volume, of 10% of oxygen and of 90% of nitrogen. This inhalation will last advantageously from 4 to 7 minutes, interrupted by pure air breathing intervals of from 2 to 3 minutes.

The duration of a training session of an athlete will preferably last for approximately 20 days.

The period of continuous inhalation of the hypoxic mixture will be progressively increased from 15 to 45 minutes each session.

During each training session, the pulse rate and blood pressure of the athlete must remain within established threshold levels, but a short duration overload, even being relatively important, should not affect his system.

During such a training session, the athlete should feel comfortable, without apparent excessive stress, and should sleep relaxed and with a normal temperature showing.

The adaptation of the user's system to the programmed loads is visualized on screen 5.

With the same device, one will be able to take care of a person suffering from cardio-vascular pathology, from an ischemic disease of the heart, by adjusting the load to the power level of 10 watts, and the speed of the crank gear to 40 rpm.

The duration of each session will be set at from 10 to 15 minutes, and the session will be reduced to 20 days, for example.

In this case, the device will be programmed so that the patient will inhale the hypoxic gas mixture during periods of from 3 to 5 minutes, interrupted by 2 to 3 minutes intervals for air breathing.

Inhalation of the hypoxic gas mixture should last for up to about 15 minutes, on the first day, then should increase progressively up to 60 minutes on the last day of treatment.

As in the first case that was described, the patient's pulse rate, blood pressure level and ECG will be monitored on screen 5.

We claim:

1. An ergometric device comprising exercising apparatus enabling a person to perform physical exercise and hypoxic gas generator means for supplying a hypoxic gas mixture to a person while exercising on said exercise apparatus, a mask to be worn by said person and a flexible hose connecting said hypoxic gas generator means with said mask, said hypoxic gas generator means comprising a cylindrical case having a side discharge opening connected by said flexible hose to said mask, a central tube extending axially of said case and having one closed end and one open end and having a plurality of openings in its side between said ends, a bundle of hollow permeable fibers in said case, said fibers extending lengthwise of said case and extending the full length of said case, said hollow fibers having the characteristics of being more permeable to one constituent gas of air than to another, closure means at opposite ends of said case for sealing spaces between said hollow fibers while leaving interiors of said hollow fibers open to the atmosphere, means for supplying air under pressure to said open end of said tube, said air flowing out of said openings in the side of said tube into said bundle of hollow fibers, a portion of a constituent gas of said air permeating walls of said hollow fibers to interiors of said hollow fibers and out through open ends of said hollow fibers while remaining constituent gases of said air flowing out through said side discharge opening of said case and through said flexible hose to said mask.

2. An ergometric device according to claims 1, further comprising control valve means for alternate supplying to said mask air and hypoxic gas from said hypoxic gas generator means.

3. An ergometric device according to claim 1, further comprising a housing for housing said hypoxic gas generator means and a display screen on said housing for displaying the pulse rate and blood pressure of a person using said exercising apparatus.

4. An ergometric device according to claim 3, further comprising on said housing programming means for programming treatment of a user of said device and for variably adjusting components of said hypoxic gas mixture.

5. An ergometric device according to claim 1, in which said hollow fibers of said hypoxic gas generating means are of poly 4-methyl-pentene-1.

6. An ergometric device according to claim 5, in which said hollow fibers have a wall thickness of 12 to 30 microns and an internal diameter of 8 to 20 microns.

* * * * *